(12) United States Patent
Kang et al.

(10) Patent No.: US 11,097,030 B2
(45) Date of Patent: *Aug. 24, 2021

(54) ADDITIVE COMPOSITIONS FOR PIGMENTED DISINFECTION AND METHODS THEREOF

(71) Applicant: Kinnos Inc., Brooklyn, NY (US)

(72) Inventors: Jason Kang, New York, NY (US); Kevin Tyan, New York, NY (US); Katherine Jin, New York, NY (US)

(73) Assignee: Kinnos, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/035,179

(22) Filed: Jul. 13, 2018

(65) Prior Publication Data

US 2019/0001010 A1    Jan. 3, 2019

Related U.S. Application Data

(63) Continuation of application No. 15/533,835, filed as application No. PCT/US2015/032325 on May 23, 2015, now Pat. No. 10,052,398.

(Continued)

(51) Int. Cl.
  *A61L 2/28*    (2006.01)
  *A61L 2/22*    (2006.01)
  (Continued)

(52) U.S. Cl.
  CPC .............. *A61L 2/28* (2013.01); *A01N 25/00* (2013.01); *A01N 33/12* (2013.01); *A01N 37/16* (2013.01); *A01N 59/00* (2013.01); *A61L 2/22* (2013.01); *C11D 1/12* (2013.01); *C11D 1/62* (2013.01); *C11D 3/044* (2013.01); *C11D 3/24* (2013.01); *C11D 3/3418* (2013.01); *C11D 3/3947* (2013.01); *C11D 3/3951* (2013.01); *C11D 3/3956* (2013.01); *C11D 3/40* (2013.01);
  (Continued)

(58) Field of Classification Search
  None
  See application file for complete search history.

(56) References Cited

U.S. PATENT DOCUMENTS 2,058,489 A    10/1936  Murch et al.
3,609,075 A *  9/1971   Barbera ................. C11D 1/342
                                               510/327

(Continued)

FOREIGN PATENT DOCUMENTS

CA    2320536 A1    3/2001
CA    2665432 A1    5/2008
(Continued)

OTHER PUBLICATIONS

International Search Report dated Sep. 10, 2015 for International Application No. PCT/US2015/032325, filed May 23, 2015.

(Continued)

*Primary Examiner* — Melissa S Mercier
(74) *Attorney, Agent, or Firm* — Elmore Patent Law Group, P.C.; Carolyn Elmore; Joseph Zucchero (57) ABSTRACT

The invention provides to a powdered composition of additives and a method of use thereof for increasing the visibility, potency and coverage of disinfectant solutions, such as bleach.

29 Claims, 2 Drawing Sheets

Related U.S. Application Data (60) Provisional application No. 62/089,183, filed on Dec. 8, 2014.

(51) Int. Cl.

| | | |
|---|---|---|
| *C11D 3/39* | (2006.01) | |
| *C11D 3/395* | (2006.01) | |
| *C11D 3/40* | (2006.01) | |
| *C11D 3/48* | (2006.01) | |
| *C11D 3/04* | (2006.01) | |
| *C11D 3/24* | (2006.01) | |
| *C11D 11/00* | (2006.01) | |
| *C11D 17/00* | (2006.01) | |
| *C11D 17/04* | (2006.01) | |
| *A01N 25/00* | (2006.01) | |
| *C11D 1/12* | (2006.01) | |
| *C11D 1/62* | (2006.01) | |
| *C11D 3/34* | (2006.01) | |
| *A01N 33/12* | (2006.01) | |
| *A01N 37/16* | (2006.01) | |
| *A01N 59/00* | (2006.01) | |

(52) U.S. Cl.
CPC ............ *C11D 3/48* (2013.01); *C11D 11/0064* (2013.01); *C11D 17/0043* (2013.01); *C11D 17/045* (2013.01)

(56) References Cited

U.S. PATENT DOCUMENTS

| | | | |
|---|---|---|---|
| 4,071,463 A * | 1/1978 | Steinhauer | C11D 1/22 252/187.26 |
| 4,229,410 A * | 10/1980 | Kosti | A61L 9/05 4/222 |
| 4,249,274 A | 2/1981 | Kitko | |
| 4,308,625 A * | 1/1982 | Kitko | A61L 9/05 4/227.6 |
| 4,346,120 A * | 8/1982 | Morley | A23C 9/137 426/565 |
| 4,353,866 A | 10/1982 | Wong | |
| 4,390,342 A | 6/1983 | Bruttel et al. | |
| 4,420,412 A | 12/1983 | Wong | |
| 4,474,677 A | 10/1984 | Foxlee | |
| 4,605,534 A * | 8/1986 | Meloy | E03D 9/038 4/227.1 |
| 4,623,476 A | 11/1986 | Nayar et al. | |
| 4,639,326 A | 1/1987 | Czempik et al. | |
| 4,678,658 A * | 7/1987 | Casey | A01N 25/06 252/408.1 |
| 4,822,854 A | 4/1989 | Ciolino | |
| 4,898,681 A * | 2/1990 | Burton | A01N 59/00 252/186.36 |
| 5,034,150 A | 7/1991 | Smith | |
| 5,064,635 A * | 11/1991 | Casey | C11D 3/40 510/100 |
| 5,110,492 A | 5/1992 | Casey | |
| 5,257,711 A | 11/1993 | Wirtz-odenthal | |
| 5,358,653 A | 10/1994 | Gladfelter et al. | |
| 5,547,662 A | 8/1996 | Khan et al. | |
| 5,556,835 A | 9/1996 | Inaoka et al. | |
| 5,670,469 A | 9/1997 | Dingus et al. | |
| 6,362,156 B1 | 3/2002 | Hsu et al. | |
| 6,447,757 B1 | 9/2002 | Orlowski et al. | |
| 6,503,877 B2 | 1/2003 | Grande et al. | |
| 6,525,237 B1 | 2/2003 | Purdon et al. | |
| 6,677,287 B1 | 1/2004 | Willman et al. | |
| 6,814,816 B2 | 11/2004 | Achar et al. | |
| 6,900,167 B2 | 5/2005 | Griese et al. | |
| 7,179,779 B1 | 2/2007 | Hauser et al. | |
| 7,271,137 B2 | 9/2007 | Tucker et al. | |
| 7,276,468 B1 | 10/2007 | Tucker | |
| 7,750,199 B1 | 7/2010 | Tucker | |
| 8,389,463 B2 | 3/2013 | Mohs et al. | |
| 9,101,134 B2 | 8/2015 | Huang et al. | |
| 9,155,310 B2 | 10/2015 | Agrawal et al. | |
| 9,458,414 B2 * | 10/2016 | Rieth | A61Q 5/10 |
| 9,717,669 B2 * | 8/2017 | Cozean | A61K 31/14 |
| 10,052,398 B2 * | 8/2018 | Kang | A01N 25/00 |
| 10,246,671 B2 | 4/2019 | Kang et al. | |
| 10,329,520 B2 | 6/2019 | Kang et al. | |
| 10,344,251 B2 | 7/2019 | Kang et al. | |
| 2001/0051567 A1 | 12/2001 | Schaschke | |
| 2003/0059483 A1 | 3/2003 | Sowle et al. | |
| 2003/0100101 A1 | 5/2003 | Huth et al. | |
| 2003/0168489 A1 | 9/2003 | Formon et al. | |
| 2004/0251375 A1 | 12/2004 | Denen et al. | |
| 2005/0019090 A1 | 1/2005 | Takasu | |
| 2006/0147482 A1 * | 7/2006 | Chang | A61K 9/0095 424/400 |
| 2008/0067470 A1 | 3/2008 | Thangaraj et al. | |
| 2008/0193650 A1 | 8/2008 | Lyon | |
| 2008/0202953 A1 | 8/2008 | Mueller et al. | |
| 2009/0032636 A1 | 2/2009 | Orlandi et al. | |
| 2009/0099054 A1 * | 4/2009 | Smith | C11D 3/046 510/293 |
| 2010/0032443 A1 | 2/2010 | Mueller et al. | |
| 2010/0069274 A1 | 3/2010 | Ebine et al. | |
| 2010/0134296 A1 | 6/2010 | Hwang | |
| 2012/0021068 A1 | 1/2012 | Barness et al. | |
| 2013/0058867 A1 | 3/2013 | Moro et al. | |
| 2013/0071488 A1 * | 3/2013 | Suekuni | C11D 17/06 424/616 |
| 2013/0100101 A1 | 4/2013 | Li et al. | |
| 2014/0057987 A1 | 2/2014 | Vinson et al. | |
| 2014/0100153 A1 * | 4/2014 | Martinez-Crowley | C11D 3/044 510/379 |
| 2015/0044144 A1 | 2/2015 | Lin et al. | |
| 2015/0093425 A1 | 4/2015 | Moore | |
| 2015/0366416 A1 | 12/2015 | Hoefte et al. | |
| 2017/0336372 A1 | 11/2017 | Kang et al. | |
| 2017/0336373 A1 | 11/2017 | Kang et al. | |
| 2018/0010080 A1 | 1/2018 | Kang et al. | |
| 2019/0001010 A1 | 1/2019 | Kang et al. | |

FOREIGN PATENT DOCUMENTS

| | | | |
|---|---|---|---|
| CA | 2865682 A1 | 3/2015 | |
| CN | 1817072 A | 8/2006 | |
| CN | 1817972 A | 8/2006 | |
| CN | 101222871 A | 7/2008 | |
| CN | 102065696 A | 5/2011 | |
| CN | 102450381 * | 5/2012 | |
| CN | 103766402 A | 5/2014 | |
| CN | 104054750 A | 9/2014 | |
| CN | 105593149 A | 5/2016 | |
| DE | 10318009 A1 | 11/2004 | |
| EP | 0018344 A1 | 10/1980 | |
| EP | 1290121 A2 | 3/2003 | |
| EP | 1457529 B1 | 9/2004 | |
| EP | 1457529 B1 | 6/2007 | |
| EP | 1846111 A2 | 10/2007 | |
| EP | 1926808 A1 | 6/2008 | |
| EP | 2170149 B1 | 10/2015 | |
| EP | 2170149 B1 | 10/2015 | |
| FR | 2988731 A1 | 10/2013 | |
| GB | 1032151 A | 6/1966 | |
| GB | 2326340 A * | 12/1998 | ............ A01N 59/00 |
| RU | 2458706 C1 | 8/2012 | |
| WO | 8201319 A1 | 4/1982 | |
| WO | 0078911 A1 | 12/2000 | |
| WO | 0123510 A2 | 4/2001 | |
| WO | 03001931 A1 | 1/2003 | |
| WO | 2004091356 A2 | 10/2004 | |
| WO | 2005055963 A2 | 6/2005 | |
| WO | 2005065509 A1 | 7/2005 | |
| WO | 2007010562 A1 | 1/2007 | |
| WO | 2008060778 A2 | 5/2008 | |
| WO | 2008147904 A2 | 12/2008 | |
| WO | 2009007924 A2 | 1/2009 | |

(56) References Cited

FOREIGN PATENT DOCUMENTS

| WO | 2013134327 A1 | 9/2013 |
|---|---|---|
| WO | 2015106044 A1 | 7/2015 |
| WO | 2016093882 A1 | 6/2016 |
| WO | 2017139670 A1 | 8/2017 |
| WO | 2018022621 A1 | 2/2018 |

OTHER PUBLICATIONS

Extended European Search Report dated Aug. 1, 2019 for European Application No. 17750892.6 filed on Feb. 10, 2017. 10 pages.
International Preliminary Report on Patentability dated Jun. 22, 2017 for International Application PCT/US2015/032325 filed May 23, 2015.
International Search Report dated Apr. 13, 2017 for International Application No. PCT/US2017017509, filed Feb. 10, 2017.
International Search Report dated Nov. 27, 2017 for International Application No. PCT/US2017/043733, filed Jul. 25, 2017.
Transcript of "Kinnos Co-Founder Jason Kang Reveals the Story Behind a Life-Saving Product", by GoDaddy, Apr. 21, 2020.
Transcript of Kevin Tyan's TedMed Talk "What if we could highlight invisible threats for our lifesavers?" Mar. 22, 2017.
Transcript of NPR interview "Innovation in the Battle Against Ebola" aired on Nov. 3, 2014.
Transcript of PBS Newshour interview "Helping student inventors turn big ideas into the next big thing" aired on Aug 31, 2016.
Transcript of UN Web TV interview "International Day of Women and Girls in Science", Feb. 10, 2017.
Written Opinion of the International Searching Authority dated Apr. 13, 2017 for International Application PCT/US2017/017509, filed Feb. 10, 2017. 13 pages.
Transcript of "Jason Kang: Ebola Design Challenge, Highlight Bleach Project," by Columbia Engineering, Apr. 1, 2015.
Transcript of "Celebrate Invention 2017," by AAAS-Lemelson Invention Ambassador Program, Aug. 7, 2017.
Transcript of "TRANS Conference 2017 Press Room Interview with Katherine Jin, Coo and Co-Founder of Kinnos," by H. Spectrum, Dec. 13, 2017.
Transcript of "Katherine Jin Explains the Evolution of Highlight," by Lemelson-MIT, Jul. 13, 2016.
Transcript of "Kinnos: E-Team Program Gives you a Chance to Think About the Business," by VentureWell, Jul. 19, 2016.
Transcript of "Jason Kang, CEO of Kinnos," featured on Cheddar, Mar. 9, 2017.
Transcript of "ScIQ Interviews: Katherine Jin and Keith Comito, Challenges in American Innovation," by ScIQ, Sep. 2, 2017.
Transcript of "Kinnos Colorized Disinfectant," Disrupt SF 2017, by TechCrunch Sep. 24, 2017.
Brickman, "All Hands on Deck", The New Yorker, Oct. 27, 2014.
Burns, "STEM Student Spotlight: Jason Kang", Scientific American Blog Network, Mar. 15, 2016.
Cooper, "Blue dye could help keep Ebola doctors safe", Engadget. com article, Oct. 13, 2016.
Farmer, M. A., Columbia Confronts the Ebola Crisis, article published on Columbia University Fu Foundation School of Engineering and Applied Science website, Oct. 17, 2014.
Kanno-Youngs, Z., "Student Invention Helps Safeguard Health-Care Workers Treating Ebola", Columbia students develop a powder that turns bleach blue to ensure fully sterilized suits, Wall Street Journal, (https://www.wsj.com/articles/student-invention-helps-safeguard-health-care-workers-treating-ebola-1464300345?cb=logged0.13334920427976615#)., May 26, 2016.

\* cited by examiner

ADDITIVE COMPOSITIONS FOR PIGMENTED DISINFECTION AND METHODS THEREOF

PRIORITY CLAIMS AND RELATED PATENT APPLICATIONS

This application is a continuation of U.S. patent application Ser. No. 15/533,835 filed on Jun. 7, 2017, which is a U.S. National Stage Entry, filed under 35 U.S.C. § 371, of International Application No. PCT/US2015/032325, filed on May 23, 2015, which claims the benefit of priority from U.S. Provisional Application Ser. No. 62/089,183, filed on Dec. 8, 2014, the contents of which are incorporated herein by reference in their entirety.

TECHNICAL FIELDS OF THE INVENTION

The invention generally relates to compositions and method for disinfection and decontamination. More particularly, the invention relates to powdered, particulate, or liquid additives and method of use thereof for increasing the visibility, potency, and coverage of disinfectant solutions.

BACKGROUND OF THE INVENTION

Timely and effective disinfection is a critical tool in controlling the spread of deadly viruses, such as the recent outbreak of Ebola in Africa. Ebola virus is highly transmittable and can remain viable on solid surfaces for several days. Bodily fluids generated by infected individuals are extremely infectious and pose great risk to both healthcare workers and the general public. Therefore, it is of critical importance to comprehensively disinfect all surfaces exposed to Ebola virus, such as personal protective equipment (PPE), transport vehicles, and surfaces in the patient care environment.

Currently, WHO protocols call for a 1:10 diluted 5.25% bleach mist to be sprayed on surfaces to kill Ebola virus, and for the bleach mist to be left on for at least 10 minutes. (Public Health Agency of Canada. (2014, Aug. 22). Retrieved from: http://www.phac-aspc.gc.ca/lab-bio/res/psds-ftss/ebola-eng.php). Especially for viruses that are transmitted through bodily fluids, it is critical that all contaminated surfaces are thoroughly covered. However, it is difficult to guarantee sufficient topical coverage because bleach is transparent. In addition, surfaces such as typical PPE suits are hydrophobic and bleach mist forms droplets upon contact, which do not fully cover the surface. Bleach droplets roll off of surfaces and therefore do not maintain the requisite 10 minutes of contact time necessary to inactive virus, leaving surfaces potentially contaminated. The WHO protocol did not prevent healthcare workers from being infected with Ebola during the recent outbreak as more than 850 healthcare personnel are known to have become infected, of whom over 500 had died.

Indeed, despite having access to protective equipment and following disinfection protocols, a CDC report suggests that healthcare workers are the group most affected by emerging infectious diseases. (Centers for Disease Control and Prevention. (2005, July). http://wwwnc.cdc.gov/eid/article/11/7/04-1038 article) For instance, during the SARS outbreak, healthcare workers comprised 21% of all cases. Similar to Ebola, the likely cause of viral transmission is the inherent difficulty of covering all infected surfaces with bleach mist and having it stay on infected areas for 10 minutes to kill the virus.

Thus, there is an urgent need for a more effective approach of disinfection that is readily usable with conventional disinfectants (e.g., bleach), allows for easy visualization without leaving stains, exhibits good stickiness to surfaces, is easily stored and transported, is safe and environmentally friendly, and is suitable for use in hospital and field settings.

SUMMARY OF THE INVENTION

The present invention is based, in part, on the discovery of a novel approach to disinfection where an additive composition is utilized with a disinfectant, such as bleach, to allow easy visualization of sprayed areas, increased surface stickiness, and exhibit excellent stability. For example, disclosed herein is a powdered or liquid additive having a pigment and a surfactant that is readily used with conventional disinfectants. The powdered or liquid additive composition is to be mixed directly with conventional disinfectant solution immediately before its use. The pigment, an oxidizable dye, initially expresses a color to provide visual confirmation of treated areas and fades to clear over time to both indicate that a sufficient amount of time has passed for adequate decontamination and to avoid staining treated surfaces.

In one aspect, the invention generally relates to a composition, which includes: a surfactant and a water-soluble pigment. The surfactant is capable of increasing the stickiness of a disinfectant solution. The water-soluble pigment is capable of colorizing a disinfectant solution, when dissolved therein, for a pre-selected time period.

In another aspect, the invention generally relates to a packet comprising the additive composition disclosed herein.

In yet another aspect, the invention generally relates to a kit including one or more packets. Each of the packets holds one or more selected from a surfactant; an alkaline builder; an oxidizing agent; a reducing agent; a hydrotrope; and a water-soluble pigment, such that, when combined, the ingredients of the one or more packets collective comprise at least one surfactant; at least one alkaline builder; at least one oxidizing agent; and at least water-soluble pigment. The water-soluble pigment is capable of colorizing a disinfectant solution, when dissolved therein, for a pre-selected time period.

In yet another aspect, the invention generally relates to an aqueous composition. The aqueous composition includes: a surfactant and a water-soluble pigment. The water-soluble pigment provides coloration for the aqueous composition for a pre-selected time period.

In yet another aspect, the invention generally relates to an aqueous composition prepared by dissolving the packets disclosed herein in an aqueous solution comprising a disinfectant.

In yet another aspect, the invention generally relates to a method for increasing the visibility, potency, and/or coverage of a disinfectant. The method includes adding the composition of disclosed herein to a solution comprising a disinfectant.

In yet another aspect, the invention generally relates to a method for increasing the visibility, potency, and/or coverage of a disinfectant. The method includes adding the one or more packets disclosed herein to a solution comprising a disinfectant.

In yet another aspect, the invention generally relates to a method for disinfecting a surface or an object. The method includes: preparing a disinfection solution that includes: a disinfectant; a surfactant; and a water-soluble pigment; and spraying the surface or object in need of disinfection. The water-soluble pigment provides coloration for the aqueous composition for a pre-selected time period. In certain embodiments, the method also includes pre-treating the pigment to alter the time of coloration.

DETAILED DESCRIPTION OF THE INVENTION

The invention provides a novel and effective approach to disinfection that is readily usable with conventional disinfectants (e.g., bleach), allows for easy visualization without leaving stains, exhibits good stickiness to surfaces, is easily stored and transported, is safe and environmentally friendly, and is suitable for use in hospital and field settings.

Because of the widespread availability of bleach solution, the method of bleach spraying for decontamination remains both prevalent and convenient. The additive compositions of the invention are especially suited for use with conventional bleach and other disinfectants and significantly increase applicability and effectiveness of the decontamination tool.

The need to add a detergent or surfactant to bleach has been well addressed. U.S. Pat. No. 4,071,463 to Steinhauer teaches the composition of a bleach formulation used for cleaning stains and discloses the use of sodium dodecyl sulfate as a detergent as well as the use of sodium hydroxide as an alkaline builder. U.S. Pat. No. 5,034,150 to Smith teaches the formulation of a stably thickened bleach solution containing a hypochlorite component, an alkyl ether sulfate surfactant, as well as an alkaline source. The addition of surfactant was found to improve the efficacy of disinfecting agents by both increasing solution viscosity and decreasing surface tension in order to increase residence time of the composition, especially on non-horizontal surfaces. Generally, the addition of an alkaline builder such as sodium hydroxide has been described to help maintain the composition pH between 11.0-14.0 in order to attain maximum hypochlorite stability. These patents involve the formulation of stable aqueous bleach solutions containing detergents, but do not disclose a powdered additive that could be used for the immediate enhancement of a bleach solution for decontamination.

The inclusion of coloring agents in aqueous bleach solutions has also been described. Due to the strong tendency of bleach solution to oxidize dyes, many have disclosed methods for the incorporation of color agents that are stable in bleach. U.S. Pat. No. 4,623,476 to Nayar teaches the method and composition for the stable suspension of pigments in aqueous hypochlorite bleach solutions, using a bleach-stable pigment (Ultramarine Blue), an optical brightener, and a surfactant. U.S. Pat. No. 6,503,877 to Grande teaches a liquid colored thickened bleach composition that includes Ultramarine Blue as a colorant and a viscosifying surfactant that helps provide stable coloration and viscosity upon prolonged periods of storage. U.S. Pat. No. 4,474,677 to Foxlee describes halogenated copper phthalocyanine pigments for forming blue or green aqueous bleaching solutions. Existing patents that involve the coloration of bleach solutions have thus far focused on compositions that ensure the stability of color upon prolonged storage. These patents have not disclosed the incorporation of bleach-sensitive dyes like FD&C Blue #1, which oxidize rapidly in bleach to allow for a temporary visual indicator of decontaminated surfaces.

For the specific purpose of surface decontamination, U.S. Pat. No. 5,670,469 to Dingus describes a composition containing a surfactant of sulfated ethoxylate alcohol, a solvent, a viscosity builder and a colored pigment such that the composition retains the original pigment color upon application to a surface. The pigment remains stable on the surface to visually express treated areas, but must be removed by scrubbing and rinsing. The patent does not disclose the use of an oxidizable pigment that can fade or disappear over time to eliminate the need for additional clean up.

Oxidizable dyes have been described before in the use of cleaning formulations. U.S. Pat. No. 4,308,625 to Kitko discloses the use of bleach-sensitive dyes in combination with hypochlorite sanitizing agents. More specifically, the disclosed invention is of a toilet bowl sanitizer in which the oxidizable dye and bleach solution are dispensed upon flushing and that the subsequent fading of the color indicates bleaching action. U.S. Pat. No. 6,447,757 to Orlowski discloses the inclusion of FD&C Blue #1 pigment as a component of a bleach-based teeth-whitening mixture. The decolorization of the dye allows the patient to monitor the occurrence and completion of teeth bleaching activity. However, these patents do not specify the use of oxidizable dyes for the application of surface decontamination and visualization of disinfectant-sprayed areas.

U.S. Pat. No. 5,110,492 to Casey discloses the combination of a cleaning composition with a disappearing pH dye that must be sealed in an air-tight container. Operating under a similar method, U.S. Pat. Application 2014/0057987 to Vinson discloses the composition of a disinfectant with a pH indicator dye and an alkaline substance. The pH dye initially expresses color upon spraying but rapidly fades to clear upon exposure to the sprayed surface and the air. These patents teach the use of a fading pH indicator dye as a method to visualize what surface has been disinfected and that a sufficient amount of time has passed to allow for disinfection. However, these patents describe a liquid preparation of disinfectant with disappearing dye and do not teach the composition or use of a powdered additive with oxidizable dye that can be used to rapidly modify bleach solutions on-site or immediately before use. Furthermore, these inventions include a pH dye that fades after 30 to 60 seconds of application, but do not describe the use of an oxidizable dye that can fade in bleach solution after prolonged periods of time.

Unlike existing disinfectants, the additive compositions of the invention do not intend to replace bleach or other disinfectant solutions; rather, the powered or liquid additives are used to enhance the potency, effectiveness and applicability of conventional disinfectants, such as the ubiquitously available bleach. The powdered or liquid additive is easily deployable on site and can be added instantly to disinfectants currently used in the field and in hospitals. Given the very mobile nature of transporting and treating infected patients, the portability of the present invention is a valuable asset.

In addition, the present invention is compatible with any spray device ranging from contractor sprays to spray bottles. Thus, implementing the present invention is advantageous, as it does not require any drastic changes in protocols, overhauls in infrastructure, or purchasing of new equipment, which is especially important for low-resource countries where infectious outbreaks are more common.

Furthermore, other colored disinfectants can cost upwards of $50 for one gallon. Typically, one contractor sprayer holds two gallons, and can be used to spray a maximum of three to four PPE suits. This creates a barrier to wide implementation of existing colored disinfectants as the majority of infectious disease outbreaks occur in low-resource countries. The cost of the present invention may be less than $1 for every two gallons of bleach solution.

Using a powder form is also advantageous because it is concentrated, so less volume is needed than a liquid additive. This makes it lightweight for transportation and reduces costs. In addition, powder is very stable with a shelf life of many years when stored properly. 5.25-8.25% bleach solutions generally lose potency after 6 weeks, while diluted bleach solutions (0.525-0.625%) degrade after 24 hours. Thus, unlike current disinfectants, a powdered additive maintains a long lifespan without sacrificing potency of the disinfectant.

Existing colored disinfectants, such as Pure Blu, are ethanol based, and evaporate too quickly to properly kill virus. In addition, the color only lasts 30-60 seconds, while spraying a suit in the field takes around five minutes. (National Forensic Science Technology Center. (2011). www.nfstc.org/?dl_id=247). Existing colored disinfectants also do not adequately adhere to and cover hydrophobic surfaces, such as PPE. Existing disinfectants that do stick to hydrophobic surfaces, such as Clorox Bleach Germicidal Cleaner, do not contain a visual indicator of sprayed areas.

The present invention addresses these issues by sustaining color for a pre-selected period of time, for example, from about 3 to about 20 minutes, which provides sufficient time to spray surfaces and ensure that all surfaces have been sprayed. One of the components is a water-soluble pigment that colorizes the bleach solution to clearly mark which surfaces have or have not been sprayed. Visualizing the bleach coverage eliminates guesswork during decontamination, reducing the likelihood that any virus remains on surfaces. It is noted that the actual time of sustained coloration may be tuned by selecting the dye and/or amount used in the composition.

Thus, in one aspect, the invention generally relates to a composition, which includes: a surfactant and a water-soluble pigment. The water-soluble pigment is capable of colorizing a bleach solution, when dissolved therein, for a pre-selected time period.

In certain embodiments, the composition further includes one or both of an alkaline builder and an oxidizing agent. In certain preferred embodiments, the composition further includes both an alkaline builder and an oxidizing agent.

In certain embodiments, the composition further includes one or both of a hydrotrope and a reducing agent. In certain preferred embodiments, the composition further includes both a hydrotrope and a reducing agent.

The water-soluble pigment is selected to oxidize and slowly lose color over a pre-selected period of time ranging from about 3 minutes to about a day (e.g., from about 3 minutes to about 18 hours, from about 3 minutes to about 12 hours, from about 3 minutes to about 6 hours, from about 3 minutes to about 3 hours, from about 3 minutes to about 1 hour, from about 3 minutes to about 45 minutes, from about 3 minutes to about 30 minutes, from about 3 minutes to about 20 minutes, from about 3 minutes to about 15 minutes, about 3 minutes to about 10 minutes, from about 5 minutes to about 30 minutes, from about 5 minutes to about 20 minutes, from about 5 minutes to about 15 minutes, about 3, 5, 8, 10, 12, 15, 18, or 20 minutes). In certain preferred embodiments, the pre-selected time period from about 5 minutes to about 15 minutes.

The water-soluble pigment may also be pre-treated to control the reaction rate of the color-fading mechanism. In certain embodiments, the water-soluble pigment is placed under ultraviolet radiation (e.g. UVA, UVB, and/or UVC) for a period of time ranging from about 1 minute to about a day. In other embodiments, the water-soluble pigment is subjected to corona and/or plasma treatment for a period of time ranging from about 5 seconds to 30 minutes.

Another ingredient is a surfactant that reduces the surface tension of the bleach solution, eliminating the formation of droplets on hydrophobic surfaces. The surfactant may also act to increase the viscosity of the solution. This allows the disinfectant solution (e.g., bleach mist) to fully cover and stick to surfaces, promoting complete topical coverage. In certain embodiments, the surfactant is specifically chosen to be effective against encapsulated viruses to enhance the potency of the disinfectant.

Any suitable surfactant may be used. Any suitable water-soluble pigment may be used. In certain preferred embodiments, the pigment is FD&C Blue #1; and the surfactant is sodium dodecyl sulfate.

Any suitable alkaline builder may be used. Any suitable oxidizing agent may be used. In certain preferred embodiments, the alkaline builder is sodium hydroxide; and the oxidizing agent is sodium nitrite.

Any suitable hydrotrope may be used. Any suitable reducing agent may be used. In certain preferred embodiments, the hydrotrope is sodium p-toluenesulfonate; and the reducing agent is ascorbic acid.

In certain preferred embodiments, the composition includes FD&C Blue #1; sodium dodecyl sulfate; sodium p-toluenesulfonate; sodium hydroxide; sodium nitrite; and ascorbic acid.

Components in the composition may have any weight percentages suitable for the intended applications. For example, weight percentages may be found in the certain ranges as follows: FD&C Blue #1 is present from about 0.0001 wt % to about 10 wt %; sodium dodecyl sulfate is present from about 0.0001 wt % to about 10 wt %; sodium p-toluenesulfonate is present from about 0.0001 wt % to about 10 wt %; sodium hydroxide is present from about 0.0001 wt % to about 10 wt %; sodium nitrite is present from about 0.0001 wt % to about 10 wt %; and ascorbic acid is present from about 0.0001 wt % to about 10 wt %, of the total weight of the composition.

It is noted that there is no limitation as to how many agents of the same type may be present in the composition. Thus, the composition may include: one or more (e.g., two, or more) thickening agents; one or more (e.g., two, or more) alkaline builders; one or more (e.g., two, or more) surfactants; one or more pigments; one or more (e.g., two, or more)

hydrotropes; one or more (e.g., two, or more) oxidizing agents; or one or more (e.g., two, or more) reducing agents.

In certain preferred embodiments, the one or more thickening agents are selected from sodium alginate, glycerol, guar gum, dextran, and cellulose.

In certain preferred embodiments, the one or more alkaline builders are selected from sodium hydroxide and potassium hydroxide.

In certain preferred embodiments, the one or more surfactants are selected from sodium dodecyl sulfate, sodium dodecylbenzenesulfonate, hexadecyltrimethylammonium bromide, and sodium 3,4-dichlorobenzoate.

In certain preferred embodiments, the one or more pigments are selected from FD&C Blue #1, fast green FCF, erythrosine, allura red AC, tartrazine, sunset yellow FCF, indigo carmine, betanin, chlorophyllin, caramel coloring, butterfly pea, pandan, ultramarine, cobalt blue, phthalocyanine, and Coomassie Brilliant Blue.

In certain preferred embodiments, the one or more hydrotrope agents are selected from sodium p-toluenesulfonate, potassium toluene-4-sulphonate, sodium xylenesulfonate, potassium xylenesulphonate, and sodium cumenesulfonate.

In certain preferred embodiments, the one or more oxidizing agents are selected from sodium nitrite, potassium nitrate, and sodium iodate.

In certain preferred embodiments, the one or more reducing agents are selected from ascorbic acid, sodium ascorbate, and glutathione.

As discussed herein, ingredients in the composition may have any weight percentages suitable for the intended applications. Weight percentages for the various types of ingredients may be found in the certain ranges as follows: thickening agents are present from about 0.0001 wt % to about 10 wt %; surfactants are present from about 0.0001 wt % to about 10 wt %; pigments are present from about 0.0001 wt % to about 10 wt %; alkaline builders are present from about 0.0001 wt % to about 10 wt %; hydrotropes are present from about 0.0001 wt % to about 10 wt %; oxidizing agents are present from about 0.0001 wt % to about 10 wt %; and reducing agents are present from about 0.0001 wt % to about 10 wt %, of the total weight of the composition.

As discussed herein, the composition is preferably in a powdery or particulate form.

In another aspect, the invention generally relates to a packet comprising the additive composition disclosed herein.

In yet another aspect, the invention generally relates to a kit including one or more packets. Each of the packets holds one or more selected from a surfactant; an alkaline builder; an oxidizing agent; a reducing agent; a hydrotrope; and a water-soluble pigment, such that, when combined, the ingredients of the one or more packets collective comprise at least one surfactant; at least one alkaline builder; at least one oxidizing agent; and at least water-soluble pigment. The water-soluble pigment is capable of colorizing a bleach solution, when dissolved therein, for a pre-selected time period.

In certain preferred embodiments, each of the ingredients is in a powdery or particulate form. In certain preferred embodiments, the packets are directly dissolvable in an aqueous bleach solution.

The unique combination of powdered ingredients may be mixed together and added at the same time, or may be added one at a time, typically with the packet having the pigment added last. In certain embodiments, the packets may be packaged in water-soluble plastic, such as PVA or PVOH, which can be dropped into a bleach solution for immediate use. In certain embodiments, one or more packets may serve as the "base" packet and another packet(s) with pigment serve as the "booster" packet. When in use, the base packet(s) may be added first with the booster packet(s) added whenever more color is needed.

In certain embodiments, compositions of the invention may be compressed to pills or tablets to facilitate dissolving at a controlled (e.g., slower) rate and to make transportation and implementation easier or suited for specific applications.

In yet another aspect, the invention generally relates to an aqueous composition. The aqueous composition includes: a surfactant and a water-soluble pigment. The water-soluble pigment provides coloration for the aqueous composition for a pre-selected time period.

In certain embodiments, the aqueous composition further includes one or both of an alkaline builder and an oxidizing agent. In certain preferred embodiments, the aqueous composition further includes both an alkaline builder and an oxidizing agent.

In certain embodiments, the aqueous composition further includes one or both of a hydrotrope and a reducing agent. In certain preferred embodiments, the aqueous composition further includes both a hydrotrope and a reducing agent.

In yet another aspect, the invention generally relates to an aqueous composition prepared by dissolving the packets disclosed herein in an aqueous solution comprising a disinfectant.

In yet another aspect, the invention generally relates to a method for increasing the visibility, potency, and/or coverage of a disinfectant. The method includes adding the composition of disclosed herein to a solution comprising a disinfectant.

In yet another aspect, the invention generally relates to a method for increasing the visibility, potency, and/or coverage of a disinfectant. The method includes adding the one or more packets disclosed herein to a solution comprising a disinfectant.

In certain preferred embodiments, the mechanism for providing coloration or discoloration for a pre-selected time period is an oxidation reaction.

As discussed herein, in certain preferred embodiments the additive composition of the invention is suited for conventional bleach, i.e., an aqueous bleach solution.

The disinfectant agent may be any suitable disinfectant compound, for example, is one or more selected from sodium hypochlorite, calcium hypochlorite, hydrogen peroxide, peracetic acid, and benzalkonium chloride.

The aqueous solution comprising a disinfectant may have any suitable pH, for example, of about 3 to about 12 (e.g., about 4 to about 12, about 5 to about 12, about 6 to about 12, about 7 to about 12, about 3 to about 10, about 3 to about 9, about 3 to about 8, about 3 to about 7, about 3 to about 5, about 5 to about 7, about 7 to about 10).

The compositions and methods of invention are effective against various viruses, bacteria and fungi. In certain embodiments, the disinfectant compositions are effective against one or more viruses. In certain embodiments, the disinfectant compositions are effective against one or more bacteria. In certain embodiments, the disinfectant compositions are effective against one or more fungi.

By way of examples, compositions and methods of invention are effective against one or more infectious agents selected from Ebola virus, West Nile virus, Marburg virus, influenza, avian influenza, canine influenza, equine influenza, swine influenza, SARS coronavirus, MERS coronavirus, Mononegavirales viruses, *E. coli, C. difficile*, cytomegalovirus, *Streptococcus pneumonia, Staphylococcus aureus,* rhinovirus, adenovirus, hantavirus, *Histoplasma capsulatum, blastomyces, Cryptococcus neoformans, Pneumocystis jiroveci,* and *Coccidioides immitis.*

In certain preferred embodiments, the disinfectant employed kills Ebola virus. In certain preferred embodiments, the disinfectant kills West Nile virus. In certain preferred embodiments, the disinfectant kills MERS coronavirus. In certain preferred embodiments, the disinfectant kills SARS coronavirus.

In yet another aspect, the invention generally relates to a method for disinfecting a surface or an object. The method includes: preparing a disinfection solution that includes: a disinfectant; a surfactant; and a water-soluble pigment; and spraying the surface or object in need of disinfection. The water-soluble pigment provides coloration for the aqueous composition for a pre-selected time period.

In certain embodiments of the method, the disinfectant solution further includes one or both of an alkaline builder and an oxidizing agent. In certain preferred embodiments, the disinfectant solution includes both an alkaline builder and an oxidizing agent.

In certain embodiments of the method, the disinfectant solution further includes one or both of a hydrotrope and a reducing agent. In certain preferred embodiments, the disinfectant solution further includes both a hydrotrope and a reducing agent.

The water-soluble pigment may provide coloration for the aqueous composition for any suitable pre-selected period of time, for example, ranging from about 3 minutes to about a day (e.g., from about 3 minutes to about 18 hours, from about 3 minutes to about 12 hours, from about 3 minutes to about 6 hours, from about 3 minutes to about 3 hours, from about 3 minutes to about 1 hour, from about 3 minutes to about 45 minutes, from about 3 minutes to about 30 minutes, from about 3 minutes to about 20 minutes, from about 3 minutes to about 15 minutes, about 3 minutes to about 10 minutes, from about 5 minutes to about 30 minutes, from about 5 minutes to about 20 minutes, from about 5 minutes to about 15 minutes, about 3, 5, 8, 10, 12, 15, 18, or 20 minutes). In certain preferred embodiments, the pre-selected time period from about 5 minutes to about 15 minutes.

The water-soluble pigment may also be pre-processed to control the reaction rate of the color-fading mechanism. In certain embodiments, the water-soluble pigment is placed under ultraviolet radiation (e.g. UVA, UVB, and/or UVC) for a period of time ranging from about 1 minute to about a day. In other embodiments, the water-soluble pigment is subjected to corona and/or plasma treatment for a period of time ranging from about 5 seconds to 30 minutes.

In certain preferred embodiments of the method, the disinfectant is bleach; the pigment is FD&C Blue #1; the surfactant is sodium dodecyl sulfate; the alkaline builder is sodium hydroxide; and the oxidizing agent is sodium nitrite. In certain preferred embodiments of the method, the hydrotrope is sodium p-toluenesulfonate; and the reducing agent is ascorbic acid.

In certain preferred embodiments, the disinfectant solution comprises FD&C Blue #1; sodium dodecyl sulfate; sodium p-toluenesulfonate; sodium hydroxide; sodium nitrite; and ascorbic acid.

In certain preferred embodiments of the method, the disinfectant solution has weight percentages as follows: bleach is present from about 0.0001 wt % to about 10 wt %; FD&C Blue #1 is present from about 0.0001 wt % to about 10 wt %; sodium dodecyl sulfate is present from about 0.0001 wt % to about 10 wt %; sodium p-toluenesulfonate is present from about 0.0001 wt % to about 10 wt %; sodium hydroxide is present from about 0.0001 wt % to about 10 wt %; sodium nitrite is present from about 0.0001 wt % to about 10 wt %; and ascorbic acid is present from about 0.0001 wt % to about 10 wt %, of the total weight of the aqueous composition.

As noted herein, there is no limitation as to how many agents of the same type may be present in the composition. Thus, in regard to the methods of the invention, the aqueous composition may include: one or more (e.g., two, or more) thickening agents; one or more (e.g., two, or more) alkaline builders; one or more (e.g., two, or more) surfactants; one or more pigments; one or more (e.g., two, or more) hydrotropes; one or more (e.g., two, or more) oxidizing agents; or one or more (e.g., two, or more) reducing agents.

As noted herein, the disinfectant agent may be any suitable disinfectant compound. In certain preferred embodiments of the method, the disinfectant agent is one or more selected from sodium hypochlorite, calcium hypochlorite, hydrogen peroxide, peracetic acid, and benzalkonium chloride. In certain preferred embodiments of the method, the one or more thickening agents are selected from sodium alginate, glycerol, guar gum, dextran, and cellulose. In certain preferred embodiments of the method, the one or more alkaline builders are selected from sodium hydroxide and potassium hydroxide. In certain preferred embodiments of the method, the one or more surfactants are selected from sodium dodecyl sulfate, sodium dodecylbenzenesulfonate, hexadecyltrimethylammonium bromide, and sodium 3,4-dichlorobenzoate. In certain preferred embodiments of the method, the one or more pigments are selected from FD&C Blue #1, fast green FCF, erythrosine, allura red AC, tartrazine, sunset yellow FCF, indigo carmine, betanin, chlorophyllin, caramel coloring, butterfly pea, pandan, ultramarine, cobalt blue, phthalocyanine, and Coomassie Brilliant Blue. In certain preferred embodiments of the method, the one or more hydrotrope agents are selected from sodium p-toluenesulfonate, potassium toluene-4-sulphonate, sodium xylenesulfonate, potassium xylenesulphonate, and sodium cumenesulfonate. In certain preferred embodiments of the method, the one or more oxidizing agents are selected from sodium nitrite, potassium nitrate, and sodium iodate. In certain preferred embodiments of the method, the one or more reducing agents are selected from ascorbic acid, sodium ascorbate, and glutathione.

As discussed herein, ingredients in the composition may have any weight percentages suitable for the intended applications. The various types of ingredients in the disinfectant solution have weight percentages as follows: thickening agents are present from about 0.0001 wt % to about 10 wt %; surfactants are present from about 0.0001 wt % to about 10 wt %; pigments are present from about 0.0001 wt % to about 10 wt %; alkaline builders are present from about 0.0001 wt % to about 10 wt %; hydrotropes are present from about 0.0001 wt % to about 10 wt %; oxidizing agents are present from about 0.0001 wt % to about 10 wt %; and reducing agents are present from about 0.0001 wt % to about 10 wt %, of the total weight of the composition.

The compositions and methods of invention are effective against various viruses, bacteria or fungi. In preferred embodiments, the compositions and methods of the invention, when applied, can result in killing 100% of one or more target viruses, bacteria and fungi in the applied surface area being disinfected. It is noted that the compositions and methods of the invention can be used effectively against encapsulated viruses, bacteria or fungi.

The compositions and methods of invention are suitable for use with various types of surfaces and objects, resulting in full coverage of the surface or object being disinfected. In preferred embodiments, upon spraying a surface or object is covered 100% by the disinfectant solution.

In certain embodiments, the pigments may be selected such that they are stable and can permanently color surfaces that do not need to be re-used.

The surface or object may be any surface or object in need of disinfection, for example, a personal protective equipment, hospital equipment, transport vehicles, buildings or structures, or personal articles.

EXAMPLES

Example 1. Bleach Additive Composition

Figure 1A:
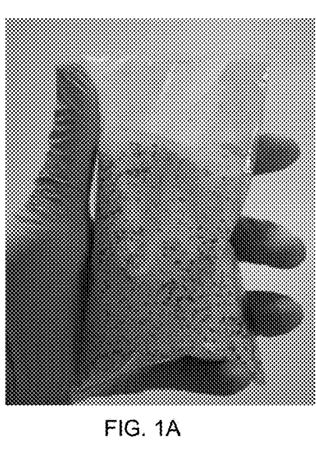
FIGS. 1A-1C. Photograph of an additive composition (powder) in lightweight packets (FIG. 1A) added to standard 1:10 diluted 5.25% bleach solution (FIG. 1B) and sprayed onto a polypropylene PPE surface (FIG. 1C).
Figure 1B:
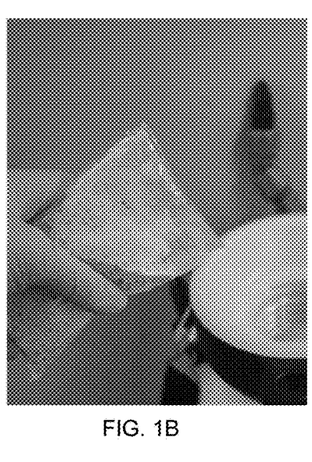
Figure 1C:
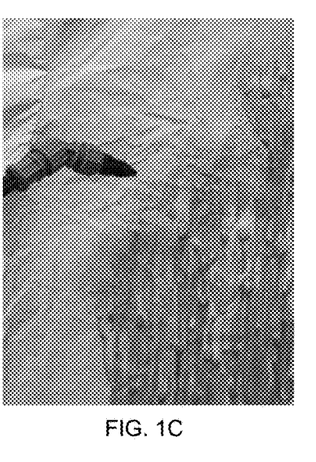

An additive composition in powder form was prepared according to the formula.

| Component | Mass (g) | % wt of 2 gallons dilute bleach |
|---|---|---|
| Sodium Dodecyl Sulfate | 151.5 | 2% |
| FD&C Blue #1 | 7.6 | 0.1% |
| Sodium Hydroxide | 7.6 | 0.1% | and packaged in lightweight packets (FIG. 1A). The additive composition was added to standard 1:10 diluted 5.25% bleach solution (FIG. 1B) and sprayed to a polypropylene PPE surface (FIG. 1C).

Figure 2A:
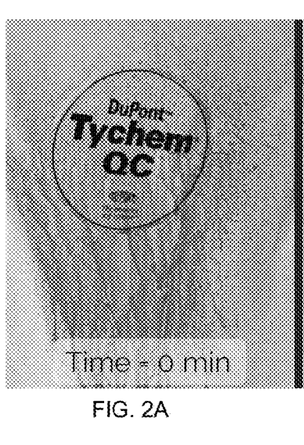
FIGS. 2A-2C. Time-lapse images showing clearance of color at 0 minutes (FIG. 2A), 7 minutes (FIG. 2B) and 15 minutes (FIG. 2C) post-spraying of the disinfection solution. An additive composition was added to bleach solution, providing coloration for up to 15 minutes upon spraying. Coloration fades clear to prevent staining and to signal to users when decontamination is complete.
Figure 2B:
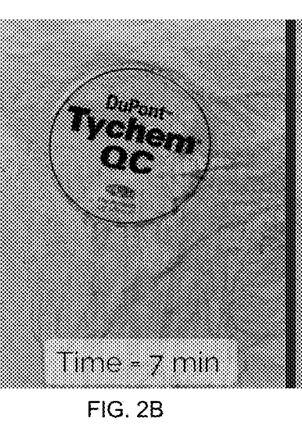
Figure 2C:
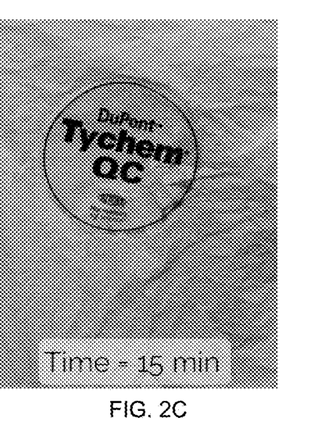

Time-lapse images were taken at time 0, 7 minutes, and 15 minutes, as shown in FIG. 2, that showed clearance of color. Additive composition was added to bleach solution for 15 minutes. Coloration fades and results in clear surface without staining, which signals to users when decontamination is complete.

Figure 3A:
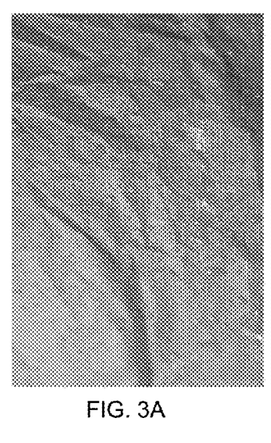
FIGS. 3A-3C. Regular bleach spray (FIG. 3A) and regular bleach spray with red dye for visualization (FIG. 3B) demonstrate droplet formation, which cause gaps in coverage, and the difficulty of visualizing regular bleach spray. Additive-enhanced bleach spray (FIG. 3C) is highly visible, does not bead up, and fully covers the surface.
Figure 3B:
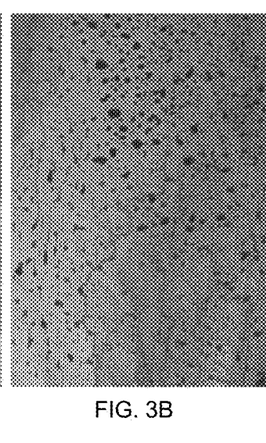
Figure 3C:
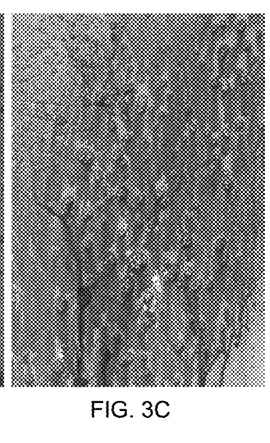

Both the regular bleach spray (FIG. 3A) and regular bleach spray with red dye for visualization (FIG. 3B) showed droplet formation with gaps in coverage clearly identifiable as well as showing difficulty of visualizing regular bleach spray. In contrast, additive-enhanced bleach spray (FIG. 3C) did not show droplet formation and the spray fully covered the target surface with easy visualization of spray.

Table 1 below shows comparative testing results. The additive-enhanced leach showed complete killing of West Nile virus. Thus, additive-enhanced bleach was just as effective in killing virus as regular bleach in tests done on West Nile virus.

TABLE 1

Efficacy of Additive-Enhanced Disinfectant on West Nile virus*

| Treatment | Virus titer [pfu/ml] | Titer reduction [log] | Percent survival [%] |
|---|---|---|---|
| Virus + buffer | $2 \times 10^6$ | N/A | 100 |
| Virus + PPE + buffer | $3 \times 10^6$ | N/A | 150 |
| Virus + PPE + Bleach | 0 | ≥6 | 0 |
| Virus + PPE + Additive Composition | 0 | ≥6 | 0 |

*West Nile virus stock was incubated for 5 min at RT with the indicated treatments, collected through washing with buffer into a centrifuge tube, spun to separate surviving virus from the disinfectant, and finally tittered by plague assay.

Example 2. Additive Compositions for Peracetic Acid-Based Disinfectants

An additive composition in power form was prepared according to the formula.

| Component | Mass (g) | % wt of 50 mL peracetic acid solution |
|---|---|---|
| FD&C Blue #1 | 0.01 | 0.02% |
| Potassium Nitrate | 0.05 | 0.1% |

In this specification and the appended claims, the singular forms "a," "an," and "the" include plural reference, unless the context clearly dictates otherwise. Unless defined otherwise, all technical and scientific terms used herein have the same meaning as commonly understood by one of ordinary skill in the art. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A method for increasing the visibility of a disinfectant solution applied to a surface or an object, the method comprising:
a) providing a disinfectant solution;
b) providing a solid or liquid composition comprising
  i) a surfactant; and
  ii) a water-soluble oxidizable pigment; and
c) mixing an amount of the composition with the disinfectant solution immediately prior to use; and
d) applying the disinfectant solution to the surface or object as a spray or film,
wherein the amount of the composition is sufficient to color the disinfectant solution, and wherein, after application to the surface or object, the color of the disinfectant solution clearly marks where the spray or film has or has not been applied to the surface or object and the color of the disinfectant solution fades to clear within a period of time.

2. The method of claim 1, wherein the period of time is from 3 to 10 minutes.

3. The method of claim 1 or 2, wherein the disinfectant solution is an aqueous bleach solution.

4. The method of claim 1 or 2, wherein the disinfectant solution comprises one or more disinfectants selected from sodium hypochlorite, calcium hypochlorite, hydrogen peroxide, peracetic acid, and benzalkonium chloride.

5. A method for disinfecting a surface or an object, comprising
  a) providing a disinfectant solution;
  b) providing a solid or liquid composition comprising
    i) a surfactant; and
    ii) a water-soluble oxidizable pigment; and
  c) mixing an amount of the composition with the disinfectant solution immediately prior to use; and
  d) applying the disinfectant solution to the surface or object as a spray or film;
  wherein the amount of the composition is sufficient to color the disinfectant solution, and wherein, after application to the surface or object, the color of the disinfectant solution clearly marks where the spray or film has or has not been applied to the surface or object and the color of the disinfectant solution fades to clear within a period of time.

6. The method of claim 1, wherein the surfactant selected from sodium dodecyl sulfate, sodium dodecylbenzenesulfonate, hexadecyltrimethylammonium bromide, and sodium 3,4-dichlorobenzoate.

7. The method of claim 1, wherein the composition further comprises a thickening agent.

8. The method of claim 1, wherein the composition further comprising a hydrotrope.

9. The method of claim 7, wherein the thickening agent is selected from sodium alginate, glycerol, guar gum, dextran, and cellulose.

10. The method of claim 8, wherein the hydrotrope is selected from sodium p-toluenesulfonate, potassium toluene-4-sulphonate, sodium xylenesulfonate, potassium xylenesulphonate, and sodium cumenesulfonate.

11. The method of claim 1, 7, or 8, wherein the surfactant comprises sodium dodecyl sulfate.

12. The method of claim 1, 7, or 8, wherein the composition further comprises an alkaline builder selected from sodium hydroxide and potassium hydroxide.

13. The method of claim 1, 7, or 8, wherein the pigment is selected from one or more of FD&C Blue #1, fast green FCF, erythrosine, allura red AC, tartrazine, sunset yellow FCF, indigo carmine, betanin, caramel coloring, butterfly pea, and Coomassie Brilliant Blue.

14. The method of claim 5, wherein the amount of the composition is sufficient to color the disinfectant solution, and wherein after application to the surface, the color of the disinfectant solution fades to clear within a period of time.

15. The method of claim 5, wherein the period of time is from 3 to 30 minutes.

16. The method of claim 15, wherein the period of time is from 3 to 10 minutes.

17. The method of claim 5 or 14, wherein the disinfectant solution is an aqueous bleach solution.

18. The method of claim 5 or 14, wherein the disinfectant solution comprises one or more disinfectants selected from sodium hypochlorite, calcium hypochlorite, hydrogen peroxide, peracetic acid, and benzalkonium chloride.

19. The method of claim 5, wherein the surfactant selected from sodium dodecyl sulfate, sodium dodecylbenzenesulfonate, hexadecyltrimethylammonium bromide, and sodium 3,4-dichlorobenzoate.

20. The method of claim 5, wherein the composition further comprises a thickening agent.

21. The method of claim 5, wherein the composition further comprising a hydrotrope.

22. The method of claim 20, wherein the thickening agent is selected from sodium alginate, glycerol, guar gum, dextran, and cellulose.

23. The method of claim 21, wherein the hydrotrope is selected from sodium p-toluenesulfonate, potassium toluene-4-sulphonate, sodium xylenesulfonate, potassium xylenesulphonate, and sodium cumenesulfonate.

24. The method of claim 5, 20, or 21, wherein the surfactant comprises sodium dodecyl sulfate.

25. The method of claim 5, 20, or 21, wherein the composition further comprises an alkaline builder selected from sodium hydroxide and potassium hydroxide.

26. The method of claim 5, 20, or 21, wherein the pigment is selected from one or more of FD&C Blue #1, fast green FCF, erythrosine, allura red AC, tartrazine, sunset yellow FCF, indigo carmine, betanin, caramel coloring, butterfly pea, and Coomassie Brilliant Blue.

27. The method of claim 5, wherein the period of time is for up to 15 minutes.

28. The method of claim 1, wherein the period of time is from 3 to 30 minutes.

29. The method of claim 1, wherein the period of time is for up to 15 minutes.

* * * * *